United States Patent
Kaminsky et al.

[11] Patent Number: 6,124,517
[45] Date of Patent: *Sep. 26, 2000

[54] OLEFIN PURIFICATION BY ADSORPTION OF ACETYLENICS AND REGENERATION OF ADSORBENT

[75] Inventors: Mark P. Kaminsky, Winfield; Shiyou Pei; Richard A. Wilsak, both of Naperville; Robert C. Whittaker, Villa Park, all of Ill.

[73] Assignee: BP Amoco Corporation, Chicago, Ill.

[ * ] Notice: This patent is subject to a terminal disclaimer.

[21] Appl. No.: 09/082,707

[22] Filed: May 21, 1998

Related U.S. Application Data

[63] Continuation-in-part of application No. 09/022,651, Feb. 12, 1998
[60] Provisional application No. 60/040,383, Mar. 10, 1997, and provisional application No. 60/046,339, May 13, 1997.

[51] Int. Cl.[7] .................................. C07C 7/00; C07C 7/12
[52] U.S. Cl. .......................... 585/829; 585/826; 585/809; 585/820
[58] Field of Search ................................... 585/809, 820, 585/829, 826

[56] References Cited

U.S. PATENT DOCUMENTS

| | | | |
|---|---|---|---|
| 2,889,893 | 6/1959 | Hess et al. | 183/114.2 |
| 3,209,050 | 9/1965 | Hanson | 260/681.5 R |
| 3,273,314 | 9/1966 | Quinn | 55/63 |
| 3,331,190 | 7/1967 | Glew et al. | 55/63 |
| 3,496,245 | 2/1970 | DeFeo et al. | 260/677 |
| 3,754,050 | 8/1973 | Duyverman et al. | 260/681.5 R |
| 3,755,488 | 8/1973 | Johnson et al. | 260/677 A |
| 3,792,981 | 2/1974 | Hettick et al. | 23/288 R |
| 3,812,057 | 5/1974 | Morgan et al. | 252/416 |
| 3,870,482 | 3/1975 | Walker et al. | 55/62 |
| 3,912,789 | 10/1975 | Frevel et al. | 260/681.5 |
| 4,019,879 | 4/1977 | Rabo et al. | 55/68 |
| 4,034,065 | 7/1977 | Kasai et al. | 423/328 |
| 4,082,694 | 4/1978 | Wennerberg et al. | 252/444 |
| 4,193,972 | 3/1980 | Pohlenz | 432/244 |
| 4,268,420 | 5/1981 | Klotz | 252/432 |
| 4,269,813 | 5/1981 | Klotz | 423/277 |
| 4,292,457 | 9/1981 | Klotz | 585/447 |
| 4,292,458 | 9/1981 | Klotz | 585/469 |
| 4,425,255 | 1/1984 | Toyoda et al. | 502/38 |
| 4,926,001 | 5/1990 | Alagy et al. | 585/500 |
| 4,992,601 | 2/1991 | Kling | 568/840 |
| 5,332,705 | 7/1994 | Huang et al. | 502/53 |

FOREIGN PATENT DOCUMENTS

| | | |
|---|---|---|
| 0132915 | 2/1985 | European Pat. Off. . |
| 2059794 | 12/1970 | Germany . |
| 61-50929 | 3/1986 | Japan . |
| 1071373 | 6/1967 | United Kingdom . |
| 1375900 | 11/1974 | United Kingdom . |
| WO9840450 | 9/1998 | WIPO . |

*Primary Examiner*—Walter D. Griffin
*Assistant Examiner*—Tam M. Nguyen
*Attorney, Agent, or Firm*—Mary Jo Kanady; Wallace L. Oliver

[57] ABSTRACT

Processes using heterogeneous adsorbents are disclosed for purification of relatively impure unsaturated hydrocarbons such as olefins, which are typically produced by thermal cracking of suitable hydrocarbon feedstocks, by passing a feed stream, containing acetylenic impurities, and, optionally, saturated hydrocarbon gases, through a particulate bed predominantly comprising a support material having high a surface area on which is dispersed at least one metallic element. Adsorption is carried out in an essentially dihydrogen-free atmosphere within the bed, effecting selective and reversible adsorption and/or complexing of the contained acetylenic contaminants with the adsorbent, thereby obtaining purified effluent which contains less than a predetermined level of the acetylenic impurities. Selective and reversible adsorption and/or complexing of the contained acetylenic impurities with the adsorbent is continued until levels of acetylenic impurities in the effluent stream increase to a predetermined level. Thereafter, the resulting bed of adsorbent is regenerated in the presence of a reducing gas containing dihydrogen to effect release of the contained acetylenic impurities from the adsorbent.

20 Claims, 1 Drawing Sheet

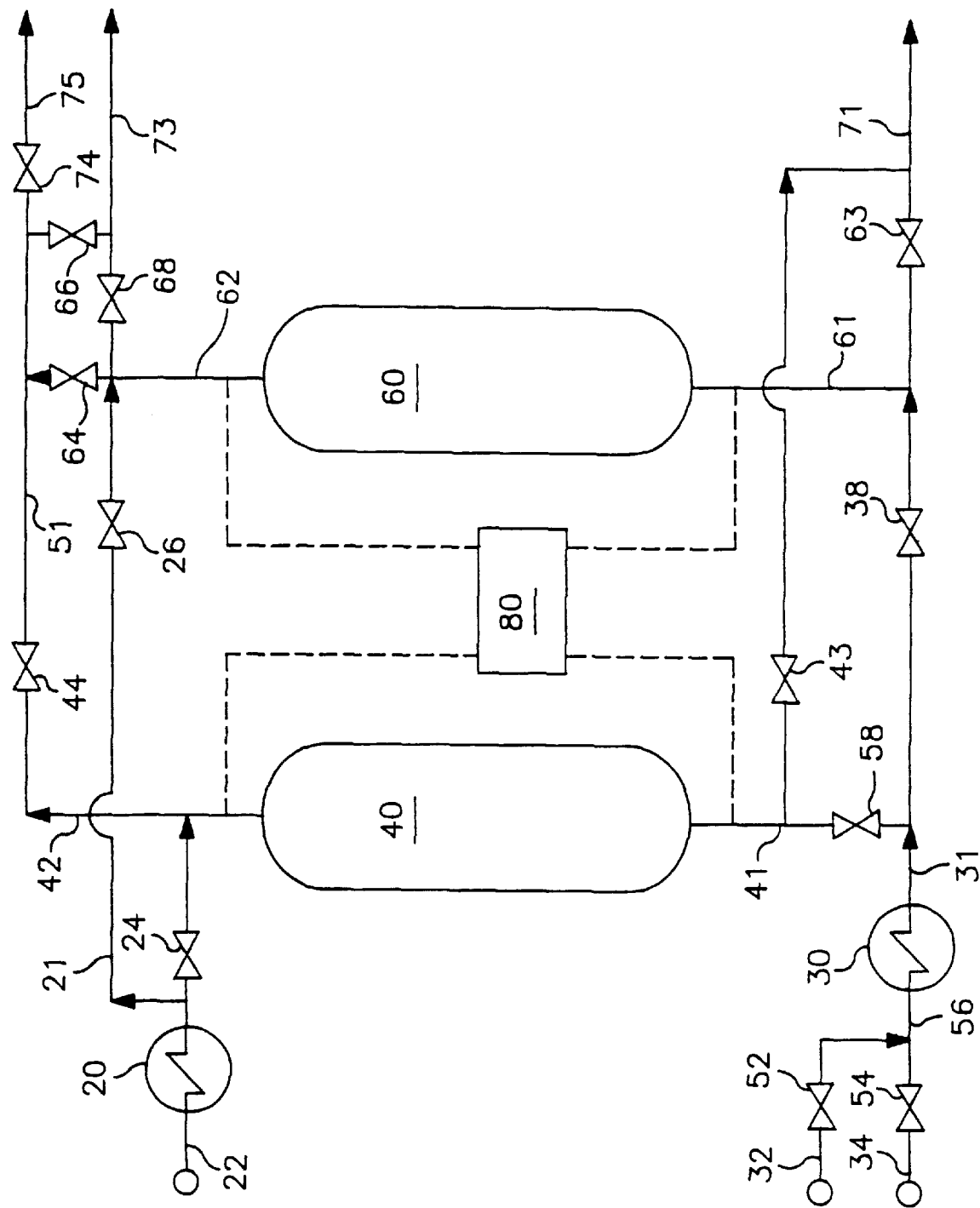

OLEFIN PURIFICATION BY ADSORPTION OF ACETYLENICS AND REGENERATION OF ADSORBENT

CROSS-REFERENCE TO RELATED APPLICATION

This application is a continuation-in-part of U.S. Ser. No. 09/022,651 filed Feb. 12, 1998, and claim the benefit of U.S. Provisional Application No. 60/040,383 filed Mar. 10, 1997, and U.S. Provisional Application No. 60/046,339 filed May 13, 1997, which applications are specifically incorporated herein in their entirety by reference.

FIELD OF THE INVENTION

The field of this invention relates to use of heterogeneous adsorbents in purification of relatively impure olefins such as are typically produced by thermal cracking of suitable hydrocarbon feedstocks. More particularly, this invention concerns purification by passing an olefinic process stream, containing small amounts of acetylenic impurities, carbon oxides and/or other organic components, which are typically impurities in cracked gas, through a particulate bed of heterogeneous adsorbent comprising a metal supported on a high surface area carrier under conditions suitable for reversible adsorption of alkynes.

Processes according to this invention are particularly useful where the olefin being purified is ethylene and/or propylene formed by thermal cracking of hydrocarbon feedstocks.

BACKGROUND OF THE INVENTION

As is well known, olefins, or alkenes, are a homologous series of hydrocarbon compounds characterized by having a double bond of four shared electrons between two carbon atoms. The simplest member of the series, ethylene, is the largest volume organic chemical produced today. Importantly, olefins including ethylene, propylene and smaller amounts of butadiene, are converted to a multitude of intermediate and end products on a large scale, mainly polymeric materials.

Commercial production of olefins is almost exclusively accomplished by pyrolysis of hydrocarbons in tubular reactor coils installed in externally fired heaters. Thermal cracking feed stocks include streams of ethane, propane or a hydrocarbon liquid ranging in boiling point from light straight-run gasoline through gas oil. Because of the very high temperatures employed, commercial olefin processes invariably coproduce significant amounts of acetylene and methyl acetylene. Required separation of the acetylene from the primary olefin can considerably increase the plant cost.

In a typical ethylene plant, the cracking represents about 25 percent of the cost of the unit, while the compression, heating, dehydration, recovery and refrigeration sections represent the remaining percentage of the total. This endothermic process is carried out in large pyrolysis furnaces with the expenditure of large quantities of heat, which is provided in part by burning the methane produced in the cracking process. After cracking, the reactor effluent is put through a series of separation steps involving cryogenic separation of products such as ethylene and propylene. The total energy requirements for the process are thus very large, and ways to reduce it are of substantial commercial interest. In addition, it is of significant interest to reduce the amounts of methane and heavy fuel oils produced in the cracking processor and utilize them for other than for their fuel value.

Hydrocarbon cracking is carried out using a feed which is ethane, propane or a hydrocarbon liquid ranging in boiling point from light straight-run gasoline through gas oil. Ethane, propane, liquid naphthas, or mixtures thereof are preferred feed to a hydrocarbon cracking unit. Hydrocarbon cracking is generally carried out thermally in the presence of dilution steam in large cracking furnaces which are heated, at least in part, by burning methane and other waste gases from the olefins process resulting in large amounts of NOx pollutants. The hydrocarbon cracking process is very endothermic and requires large quantities of heat per pound of product. However, newer methods of processing hydrocarbons utilize, at least to some extent, catalytic processes which are better able to be tuned to produce a particular product slate. The amount of steam used per pound of feed in the thermal process depends to some extent on the feed used and the product slate desired. Typically, steam pressures are in the range of about 30 lbs per sq in to about 80 lbs per sq in (psi), and amounts of steam used are in the range of about 0.2 pounds of steam per pound of feed to 0.7 pounds of steam per pound of feed. The temperature, pressure and space velocity ranges used in thermal hydrocarbon cracking processes depend to some extent upon the feed used and the product slate desired, which are well known and may be appreciated by one skilled in the art.

The type of furnace used in the thermal cracking process is also well known. However the ceramic honeycomb furnace which is described in U.S. Pat. No. 4,926,001, the contents of which patent are specifically incorporated herein by reference, is an example of a new type of cracking which could have a special utility for this process.

Several methods are known for separation of an organic gas containing unsaturated linkages from gaseous mixtures. These include, for instance, cryogenic distillation, liquid adsorption, membrane separation and the so called "pressure swing adsorption" in which adsorption occurs at a higher pressure than the pressure at which the adsorbent is regenerated. Cryogenic distillation and liquid adsorption are common techniques for separation of carbon monoxide and alkenes from gaseous mixtures containing molecules of similar size, e.g. nitrogen or methane. However, both techniques have disadvantages such as high capital cost and high operating expenses. For example, liquid adsorption techniques suffer from solvent loss and need a complex solvent make-up and recovery system.

Molecular sieves which selectively adsorb carbon monoxide from gaseous mixtures by chemisorption are also known. U.S. Pat. No. 4,019,879 and U.S. Pat. No. 4,034,065 refer to use of high silica zeolites, which have relatively high selectivities for carbon monoxide, in the pressure swing adsorption method. However, these zeolites only have moderate capacity for carbon monoxide, and more particularly require very low vacuum pressures to recover the adsorbed gases and/or to regenerate the zeolite.

U.S. Pat. No. 4,717,398 describes a pressure swing adsorption process for selective adsorption and subsequent recovery of an organic gas containing unsaturated linkages from gaseous mixtures by passing the mixture over a zeolite ion-exchanged with cuprous ions (Cu I) characterized in that the zeolite has a faujasite type crystalline structure (Y).

Kokai JP Number 50929-1968 describes a method of purifying vinyl compounds containing up to about 10 percent by weight of acetylenic compounds. In this method, acetylenic compounds were described as being adsorbed on an adsorption agent of 1-valent and/or 0-valent copper and/or silver supported on inert carrier such as δ-alumina, silica or active carbon. Separations described included 1000 ppm ethyl acetylene and 1000 ppm vinyl acetylene from liquid 1,3-butadiene, 100 ppm acetylene from ethylene gas, 100 ppm methyl acetylene from propylene gas, and 50 ppm phenyl acetylene from liquid styrene (vinylbenzene). Each application used fresh adsorption agent and only a short time of one hour on stream at mild conditions of temperature and pressure. Such limited applications were likely because it is well known that acetylene and these acetylene compounds react with copper and/or silver to form copper acetylide or silver acetylide. Both the acetylide of copper and silver are unstable compounds. Because they are explosive under some conditions, their possible formation presents safety problems in operation and in handling adsorbent containing such precipitates.

More recently, German Disclosure Document 2059794 describes a liquid adsorption process for purification of paraffinic, olefinic and/or aromatic hydrocarbons with an adsorption agent consisting in essence of a complex of a copper (Cu I)-salt with an alkanolamine such as monoethanolamine, monoisopropanolamine, diethanolamine, triethanolamine and arylalkanolmines, and optionally in the presence of a glycol or polyglycol. However, the product stream is contaminated with unacceptable levels of components of such agents absorbed in the hydrocarbon flow. While such contamination might be removable using an additional bed of silica gel, aluminum oxide or a wide-pored molecular sieve, this would involve additional capital costs, operation expenses and perhaps safety problems.

Olefin-paraffin separations represent a class of most important and also most costly separations in the chemical and petrochemical industry. Cryogenic distillation has been used for over 60 years for these separations. They remain to be the most energy-intensive distillations because of the close relative volatilities. For example, ethane-ethylene separation is carried out at about −25° C. and 320 pounds per square inch gage pressure (psig) in a column containing over 100 trays, and propane-propylene separation is performed by an equally energy-intensive distillation at about −30° C. and 30 psig.

Impurity refers to compounds that are present in the olefin plant feedstocks and products. Well-defined target levels exist for impurities. Common impurities in ethylene and propylene include acetylene, methyl acetylene, methane, ethane, propane, propadiene, and carbon dioxide. Listed below are the mole weight and atmospheric boiling points for the light products from thermal cracking and some common compounds potentially found in an olefins unit. Included are some compounds which have similar boiling temperatures to cracked products and may be present in feedstocks or produced in trace amounts during thermal cracking.

| Compound | Mole Weight | Normal Boiling Point, ° C. |
| --- | --- | --- |
| Hydrogen | 2.016 | −252.8 |
| Nitrogen | 28.013 | −195.8 |
| Carbon monoxide | 28.010 | −191.5 |
| Oxygen | 31.999 | −183.0 |
| Methane | 16.043 | −161.5 |
| Ethylene | 28.054 | −103.8 |
| Ethane | 30.070 | −88.7 |
| Phosphine | 33.970 | −87.4 |
| Acetylene* | 26.038 | −84.0 |

-continued

| Compound | Mole Weight | Normal Boiling Point, ° C. |
| --- | --- | --- |
| Carbon dioxide* | 44.010 | −78.5 |
| Radon | 222.00 | −61.8 |
| Hydrogen sulfide | 34.080 | −60.4 |
| Arsine | 77.910 | −55.0 |
| Carbonyl sulfide | 60.070 | −50.3 |
| Propylene | 42.081 | −47.8 |
| Propane | 44.097 | −42.1 |
| Propadiene (PD) | 40.065 | −34.5 |
| Cyclo-propane | 42.081 | −32.8 |
| Methyl acetylene | 40.065 | −23.2 |
| Water | 18.015 | 100.0 |

*Sublimation temperature

Recently, the trend in the hydrocarbon processing industry is to reduce commercially acceptable levels of impurities in major olefin product streams, i.e., ethylene, propylene, and hydrogen. Need for purity improvements is directly related to increasing use of higher activity catalysts for production of polyethylene and proypropylene, and, to a limited, extent other olefin derivatives.

It is known that acetylenic impurities can be selectively hydrogenated and thereby removed from such product streams by passing the product stream over an acetylene hydrogenation catalyst in the presence of dihydrogen (molecular hydrogen, $H_2$). However, these hydrogenation processes typically result in the deposition of carbonaceous residues or "green oil" on the catalyst which deactivates the catalyst. Therefore, acetylene hydrogenation processes for treating liquid or liquefiable olefins and diolefins typically include an oxygenation step or a "burn" step to remove the deactivating carbonaceous residues from the catalyst, followed by a hydrogen reduction step to reactivate the hydrogenation catalyst. For example, see U.S. Pat. No. 3,755,488 to Johnson et al., U.S. Pat. No. 3,792,981 to Hettick et al., U.S. Pat. No. 3,812,057 to Morgan and U.S. Pat. No. 4,425,255 to Toyoda. However, U.S. Pat. Nos. 3,912,789 and 5,332,705 state that by using selected hydrogenation catalysts containing palladium, at least partial regeneration can be accomplished using a hydrogenation step alone at high temperatures (600° to 700° F.) and in the absence of an oxygenation step.

Selective hydrogenation of the about 2000 to 4000 parts per million of acetylenic impurities to ethylene is generally a crucial operation for purification of olefins produced by thermal steam cracking. Typical of a small class of commercially useful catalysts are materials containing very low levels of an active metal supported on an inert carrier, for example a particulate bed having less than about 0.03 percent (300 ppm) palladium supported on the surface skin of carrier pellets having surface area of less than about 10 $m^2/gm$.

Many commercial olefin plants using steam crackers use front-end acetylene converters, i.e. the hydrogenation unit is fed $C_3$ and lighter cracked gas, which feed has a high enough concentration of hydrogen to easily hydrogenate the acetylenic impurities; however, when run improperly, will also hydrogenate a large fraction of the ethylene and propylene product. Both hydrogenation of acetylene and ethylene are highly exothermic as shown below:

$C_2H_2 + H_2 \rightarrow C_2H_4$     H = −41 kcal/mole
$C_2H_4 + H_2 \rightarrow C_2H_6$     H = −32.7 kcal/mole Accelerated catalyst deactivation and thermal runaways caused by loss in catalyst selectivity are common problems which plague acetylene converters. Such problems result in unscheduled shutdowns and increased costs to replace deactivated catalyst.

The problem of over-hydrogenation is aggravated because the rate constant for ethylene hydrogenation to ethane is 100 times faster than for the hydrogenation of acetylene to ethylene. As a means to avoid a $C_2H_4$ hydrogenation thermal runaway, acetylene, carbon monoxide and diolefins concentrations must be high enough to cover most active sites so none are left to adsorb ethylene. For example, acetylene, carbon monoxide, methyl acetylene, and propadiene have bond strengths to palladium which are stronger than the ethylene to palladium bonds. Selection of active metal, size of the metal particles and other physical and chemical factors ultimately affect the "operating temperature window" which is the delta of temperature between acetylene conversion to ethylene (typically in a range from about 100° F. to about 150° F.) and thermal runaway where all molecular hydrogen is converted and a large amount of the ethylene is converted to ethane (about 170° F. to about 225° F.). The wider the window, the safer is operation of the unit.

It is therefore a general object of the present invention to provide an improved process which overcomes the aforesaid problem of prior art methods for production of unsaturated hydrocarbons, e.g. olefins, from thermal cracking of hydrocarbon feed stocks, which olefin can be used for manufacture of polymeric materials using higher activity catalysts.

More particularly, it is an object of the present invention to provide an improved method for purification of ethylene and/or propylene containing small amounts of acetylenic impurities, carbon oxides and/or other organic components that are impurities in olefinic process streams, by passing the impure olefin stream through a particulate bed of heterogeneous adsorbent comprising a metal, supported on a high surface area carrier, under conditions suitable for reversible adsorption of alkynes.

It is another object of the present invention to provide an improved aforesaid purification method that employs an adsorbent that, even after a substantial period of aging, exhibits an ability to withstand frequent regenerations and yet retain useful adsorption capacity.

It is further an object of this invention to provide an improved process for regeneration of adsorbent loaded with acetylenic impurities.

Other objects and advantages of the invention will become apparent upon reading the following detailed description and appended claims.

SUMMARY OF THE INVENTION

Economical processes are disclosed for purification of relatively impure unsaturated hydrocarbons, e.g., olefins produced by thermal cracking of hydrocarbons. Processes of this invention comprise; passing a mixture comprising an unsaturated hydrocarbon compound of from 2 to about 8 carbon atoms, including at least one vinyl group, acetylenic and diolefin (alkadienes) impurities having the same or similar carbon content, and, optionally, saturated hydrocarbon gases through a particulate bed of adsorbent predominantly comprising a support material having high surface area on which is dispersed at least one metallic element selected from the group consisting of copper and silver, to effect, in the presence of an essentially dihydrogen-free atmosphere within the bed, selective and reversible adsorption and/or complexing of the contained acetylenic contaminants with the adsorbent, thereby obtaining purified effluent which contains less than a predetermined level of the acetylenic impurities; and, thereafter, regenerating the resulting bed of adsorbent in the presence of a reducing gas comprising dihydrogen (molecular hydrogen) to effect release of the contained acetylenic impurities from the adsorbent.

Another aspect of special significance is the separation of acetylenic impurities from a gaseous mixture of ethylene or propylene containing small amounts of acetylene, i.e. less than about 5000 parts per million by weight of one or more acetylenic impurities, and advantageously provide purified product containing less than about 1 part per million by weight, and frequently even less than about 0.5 parts per million by weight of acetylenic impurities.

In yet another aspect, the invention is a process for purification of olefins produced by thermal cracking of hydrocarbons which comprises: passing a gaseous mixture comprising at least about 99 percent by volume of an olefin having two to about four carbon atoms, and acetylenic impurities having the same or similar carbon content in an amount ranging upward from about 1 to about 1000 parts per million by volume, through a particulate bed of adsorbent predominantly comprising a support material selected from the group alumina, silica, active carbon, clay and zeolites, having a surface area in a range of from about 10 to about 2,000 square meters per gram as measured by the BET gas adsorption method, on which is dispersed at least one metallic element selected from the group consisting of copper and silver having particles of average diameter in a range of less than about 500 Angstroms, to provide an effluent stream from the bed; effecting, in the presence of an essentially dihydrogen-free atmosphere within the bed, selective and reversible adsorption and/or complexing of the contained acetylenic impurities with the adsorbent, until levels of the acetylenic impurities in the effluent stream increase to a predetermined level in a range downward from about 1 part per million by volume; and, thereafter, regenerating the resulting bed of adsorbent in the presence of a reducing gas, preferably comprising dihydrogen, to effect release of the contained acetylenic impurities from the adsorbent.

For a more complete understanding of the present invention, reference should now be made to the embodiments illustrated in greater detail in the accompanying drawing and described below by way of examples of the invention.

BRIEF DESCRIPTION OF THE FIGURE

The appended claims set forth those novel features which characterize the present invention. The present invention itself, as well as advantages thereof, may best be understood, however, by reference to the following brief description of preferred embodiments taken in conjunction with the annexed drawing in which:

The FIGURE is a schematic diagram of a preferred method for operating the process of this invention in the continuous mode, being arranged to provide sufficient reactants for the reactions and to maintain suitable reaction temperatures in accordance with the present invention.

BRIEF DESCRIPTION OF THE INVENTION

Processes of this invention are particularly suitable for use in purification of unsaturated hydrocarbon compounds of from 2 to about 8 carbon atoms which include at least one vinyl group, e.g. aliphatically unsaturated organic compounds generally produced by thermal cracking of hydrocarbons.

Compounds of most interest with regard to purification by the method of the present invention have two to about eight carbon atoms, preferably two to about four carbon atoms, and more preferably ethylene or propylene. The separation of acetylenic impurities from ethylene or propylene which may be contained in admixtures with other normally gaseous materials, such as one or more of ethane, methane, propane and oxides of carbon, is of particular importance. For example, mixtures serving as a source of ethylene-containing feed for the process may contain about 1 to about 99 weight percent ethylene, about 0 to about 50 weight percent ethane, and/or about 0 to about 50 weight percent methane.

Generally, acetylenic impurities described in this invention are expressed by the formula

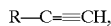

where R is hydrogen or a hydrocarbon group of up to 10 carbon toms.

It is desirable to treat the gaseous mixture used in the process of the present invention to remove any gaseous hydrogen and/or carbon monoxide. The amount of hydrogen in the gaseous mixture should suitably be reduced to below 10 parts per million by weight, preferably below 2 parts per million by weight, and most preferably below 1 part per million by weight, prior to contact with the adsorbent.

Similarly, any mercury-containing, arsenic-containing, and sulfur-containing components, e.g. hydrogen sulfide, present in the gaseous mixture fed to the particulate bed of adsorbent should suitably be removed therefrom in any known manner in order to avoid the risk of poisoning the dispersed metal. The hydrocarbon mixture used in the process of the present invention is suitably a cracked gas from which the majority of the $C_5$ and higher hydrocarbons have been removed. The gaseous mixture may thus comprise ethylene, propylene, butenes, methane, ethane, propane and butane. Small amounts of pentanes and pentenes can be tolerated in the gaseous mixture.

In preferred embodiments of processes according to the invention, the olefin in the gaseous mixture being purified is predominantly ethylene or propylene, the gaseous mixture contains less than about 0.5 parts per million by volume of hydrogen and less than about 1 part per million by volume of mercury-containing, arsenic-containing, and sulfur-containing components, each calculated as the element, and wherein the gaseous mixture, while passing through the bed, is at temperatures in a range upward from about −78° C. to about 100° C., preferably in a range of from about −35° C. to about 65° C., and more preferably in a range of from about −10° C. to about 55° C.

The gaseous mixture used in the process of the present invention may also comprise water and may optionally be saturated with water.

Broadly, according to the present invention, there is provided a particulate bed of adsorbent comprising predominantly a support material having high surface area on which is dispersed at least one metallic element selected from the group consisting of copper, silver, iron, cobalt, nickel, zinc, ruthenium, palladium, platinum, and potassium, preferably at least one metallic element selected from the group consisting of copper and silver. Suitable adsorbents exhibit, in the presence of an essentially dihydrogen-free atmosphere within the bed, selective and reversible adsorption and/or complexing of the acetylenic impurities with the adsorbent. According to the present invention, dispersed metal content is in a range of from about 0.01 to about 40 percent based on the total weight of the adsorbent. Preferably, dispersed metal content is in a range of from about 0.01 to about 20 percent based on the total weight of the adsorbent.

Suitable sources of the metallic elements include inorganic acid salts, organic acid salts and metallic oxides. Preferred sources of dispersed metal are soluble compounds, more preferred water soluble compounds such as metallic nitrates.

Preferred for processes, according to this invention, are adsorbents wherein the metallic element is dispersed on the high surface area support material in particles having average diameter in a range of less than about 500 Angstroms, preferably in a range of less than about 200 Angstroms, and more preferably in a range of less than about 100 Angstroms. Average diameters of small dispersed metal particles are measured by a method using the broadening of lines in an X-ray powder diffraction pattern. Such particle size measurement is discussed in Anthony R. West's *Solid State Chemistry and its Application*, p. 51 and p. 173–175 John Wiley & Sons Ltd. (1984).

A preferred class of adsorbents useful in processes according the invention, comprises at least about 90 weight percent of a gamma alumina having surface area in a range of from about 80 to about 500 square meters per gram as measured by the BET gas adsorption method, and contains less than 500 parts per million by weight of a sulfur-containing component, calculated as elemental sulfur. More preferred are the adsorbents which comprise at least about 90 weight percent of a gamma alumina having surface area in a range of from about 150 to about 350 square meters per gram as measured by the BET gas adsorption method, and wherein the metal dispersed on the support material is copper, and the adsorbent has a copper content in a range of from about 0.01 to about 10 percent based on the total weight of the adsorbent.

The adsorbent can optionally further comprise one or more elements selected from the group consisting of lithium, sodium, potassium, zinc, molybdenum, tin, tungsten, and iridium, dispersed on the support material. Preferably the adsorbent further comprises a member selected from the group consisting of lithium, sodium, potassium, zinc, molybdenum, and tin dispersed on the support material.

For processes according to the invention the metal dispersed on the support material is advantageously at least one element selected from the group consisting of iron, cobalt, nickel, and palladium, and the adsorbent has a dispersed metal content in a range of from about 0.05 to about 20 percent based on the total weight of the adsorbent.

Another class of adsorbents useful for processes according to the invention comprises a dispersion of copper or silver, and one metallic element selected from the group consisting of lithium, sodium, potassium, zinc, molybdenum, tin, tungsten, and iridium, dispersed on the support material.

More preferred for processes, according to this invention, are adsorbents having copper metal dispersed on the support, and the adsorbent has a copper content in a range of from about 0.05 to about 10 percent, more preferred in a range of from about 0.1 to about 5.0 percent, based on the total weight of the adsorbent.

High metal dispersion and loading resulted in higher metal surface area. Capacity of an adsorbent is typically related directly to metal surface area. Any method which increases and/or maintains high metal surface area is, therefore, beneficial to achieving high acetylene adsorption capacity.

Preferred for processes according to this invention are adsorbents having a dispersion value of at least about 10 percent, preferably in a range upward from about 20 percent to about 80 percent. Dispersion is a measure of the accessibility of the active metals on the adsorbent. Such dispersion methods are discussed in H. C. Gruber's, *Analytical Chemistry*, Vol. 13, p. 1828, (1962). The adsorbents for use in this invention were analyzed for dispersion using a pulsed carbon monoxide technique as described in more detail in the Examples. Palladium-containing adsorbents having large dispersion values are desired because more of the palladium metal is available for reaction.

Support materials are advantageously selected from the group consisting of alumina, silica, carbon, clay and zeolites (molecular sieves). Surface areas of support materials are preferably in a range of from about 10 to about 2,000 square meters per gram as measured by the BET gas adsorption method.

A preferred class of active carbons useful herein are materials disclosed in commonly assigned U.S. Pat. No. 4,082,694 to Arnold N. Wennerberg and Thomas M. O'Grady, which patent is incorporated herein by reference. Such suitable active carbon products are produced from carbonaceous material by a staged temperature process which provides improved yield and processability during manufacture. A source of carbonaceous material, such as crushed coal, coal coke, petroleum coke or a mixture thereof, is heated with agitation in the presence of a substantial weight ratio of potassium hydroxide at a first lower temperature to dehydrate the combination. Thereafter the temperature is raised to a second higher temperature to activate the combination which is thereafter cooled and washed to remove inorganic matter and form a high surface area active carbon having a cage-like structure exhibiting micro-porosity, good bulk density and Total Organic Carbon Index.

Active carbon products for use as supports, according to this invention, preferably have an effective surface area greater than about 2,300 square meters per gram, and more preferably greater than about 2,700 square meters per gram, and most preferably above about 3,000 square meters per gram as measured by the BET method. Active carbon products for use as supports typically have a bulk density greater than about twenty-five hundredths gram per cubic centimeter, and preferably greater than about twenty-seven hundredths gram per cubic centimeter, and more preferably above about three-tenths gram per cubic centimeter. Further, useful active carbon products preferably have a Total Organic Carbon Index greater than about 300, more preferably greater than about 500, and most preferably greater than about 700.

Generally, the term "molecular sieve" includes a wide variety of positive-ion-containing crystalline materials of both natural and synthetic varieties. They are generally characterized as crystalline aluminosilicates, although other crystalline materials are included in the broad definition. The crystalline aluminosilicates are made up of networks of tetrahedra of $SiO_4$ and $AlO_4$ moieties in which the silicon and aluminum atoms are cross-linked by the sharing of oxygen atoms. The electrovalence of the aluminum atom is balanced by the use of positive ions such as, for example, alkali-metal or alkaline-earth-metal cations.

Zeolitic materials, both natural and synthetic, useful herein, have been demonstrated in the past to have catalytic capabilities for many hydrocarbon processes. Zeolitic materials, often referred to as molecular sieves, are ordered, porous, crystalline aluminosilicates having a definite structure, with large and small cavities interconnected by channels. The cavities and channels throughout the crystalline material are generally uniform in size, allowing selective separation of hydrocarbons. Consequently, these materials in many instances have come to be classified in the art as molecular sieves and are utilized, in addition to the selective adsorptive processes, for certain catalytic properties.

The catalytic properties of these materials are also affected to some extent by the size of the molecules which are allowed to selectively penetrate the crystal structure, presumably to be contacted with active catalytic sites within the ordered structure of these materials.

In the past various natural and synthetic molecular sieve compositions have been found to be useful for a number of hydrocarbon conversion reactions. Among these are alkylation, aromatization, dehydrogenation and isomerization. Among the sieves which have been used are Type A, X, Y and those of the MFI crystal structure as shown in "Atlas of Zeolite Structure Types," Second Revised Edition, 1987, published on behalf of the Structure Commission of the International Zeolite Associates, and incorporated by reference herein. Representative of the last group are ZSM-5 and AMS borosilicate molecular sieves.

Prior art developments have resulted in the formation of many synthetic crystalline materials. Crystalline aluminosilicates are the most prevalent and, as described in the patent literature and in the published journals, are designated by letters or other convenient symbols. Exemplary of these materials are Zeolite A (Milton, in U.S. Pat. No. 2,882,243), Zeolite X(Milton, in U.S. Pat. No. 2,882,244), Zeolite Y(Breck, in U.S. Pat. No. 3,130,007), Zeolite ZSM-5 (Argauer et al., in U.S. Pat. No. 3,702,886), Zeolite ZSM-II (Chu, in U.S. Pat. No. 3,709,979), Zeolite ZSM-12 (Rosinski et al., in U.S. Pat. No. 3.832,449), and others.

Manufacture of the ZSM materials utilizes a mixed base system in which sodium aluminate and a silicon-containing material are mixed together with sodium hydroxide and an organic base, such as tetrapropylammonium hydroxide and tetrapropylammonium bromide, under specified reaction conditions to form the crystalline aluminosilicate, preferably a crystalline metallosilicate exhibiting the MFI crystal structure.

A preferred class of molecular sieves useful according to the present invention are crystalline borosilicate molecular sieves disclosed in commonly assigned U.S. Pat. Nos. 4,268,420, 4,269,813, 4,292,457, and 4,292,458 to Marvin R Klotz, which are incorporated herein by reference.

BRIEF DESCRIPTION OF PREFERRED EMBODIMENTS OF THE INVENTION

While this invention is susceptible to embodiment in many different forms, this specification and accompanying drawing disclose only some specific forms as an example of the use of the invention. In particular, preferred embodiments of the invention for purification of a gaseous mixture comprising olefin preferably an olefin of from two to about eight carbon atoms having a single double bond, acetylenic impurities having the same or similar carbon content, and, optionally, alkanes (paraffin hydrocarbons) and/or alkenes having more than one double bond (di- or tri-olefin hydrocarbons) produced by thermal cracking of hydrocarbons, are illustrated and described. The invention is not intended to be limited to the embodiments so described, and the scope of the invention will be pointed out in the appended claims.

The apparatus of this invention is used with certain conventional components, the details of which, though not fully illustrated or described, will be apparent to those having skill in the art and an understanding of the necessary function of such components.

More specifically with reference to the FIGURE, a preferred embodiment of the invention is an integrated olefin purification system including: one or more optional heat exchangers for controlling temperature of the gaseous feedstream to temperatures in a range from about −20° F. to about 200° F., illustrated as feed exchanger 20; adsorption vessels containing particulate beds of a suitable solid adsorbent, illustrated as vessels 40 and 60; and means for analysis of feed and effluent streams, illustrated as on-line analytical system 80.

During operation of the integrated olefin purification system, a gaseous mixture containing less than about 500 parts per million by weight of the acetylene and carbon monoxide impurities formed by chemical conversions in commercial thermal cracking processes, is, for example, ethylene fed from the overhead of a C2 distillation tower or intermediate storage (not shown) through conduit 22 and into feed exchanger 20 to control temperature during adsorption. Effluent from feed exchanger 20 flows through manifold 21 or, alternately, through valve 24 and manifold 42, or valve 26 and manifold 62, into one of two adsorption vessels 40 and 60 which contain beds of suitable solid adsorbent such as gamma alumina with 1.0 percent palladium based upon the weight of adsorbent.

During operation, the gaseous mixture passes through the bed of particulate adsorbent at gas hourly space velocities in a range of from about 0.05 hours$^{-1}$ to about 20,000 hours$^{-1}$ and higher, preferably from about 0.5 to about 10,000 hours$^{-1}$.

Compositions of the gaseous feed and effluent of each adsorption vessel is monitored by on-line analytical system 80. While levels of acetylenic impurities in the effluent of the adsorption vessel in purification service are in a range downward from a predetermined level, purified olefin from adsorption vessel 40 and/or adsorption vessel 60 flows through manifold 41, valve 43 and/or manifold 61 and valve 63, then through manifold 71 directly to pipeline for transportation of polymer grade ethylene, or to storage (not shown). When the level of acetylenic impurities in the effluent of an adsorption vessel in purification service reaches or exceeds the predetermined level, purified olefin flowing through manifold 71 is diverted to flare (not shown) while that adsorption vessel is isolated from the process flow by means of valve 24 and valve 43, or valve 26 and 63, and thereafter the resulting bed of loaded adsorbent is treated to effect release of the contained acetylenic impurities from the adsorbent by hydrogenation.

Suitable adsorbents have a capacity to treat from about 300 to about 40,000 pounds of olefin feed per pound of adsorbent where the olefin feed contains about 0.5 parts per million (ppm) acetylene. Approximately 5×10$^{-4}$ pounds of acetylene to about 1×10$^{-2}$ pounds are advantageously adsorbed per pound of adsorbent before regeneration is required.

During continuous operation of this embodiment, the time required for alternately treating the loaded adsorbent to effect release of the contained acetylenic impurities from the adsorbent by hydrogenation is provided by using two (as shown) or more independent adsorption vessels containing beds. Regenerations are advantageously performed according to this invention in three steps.

At the end of each bed's adsorption cycle, the adsorption vessel which contains the loaded bed, for example vessel 60, is isolated from the process flow by means of valve 26 and valve 63, and depressured through manifold 62, valve 64, and manifold 51 to suitable disposal, such as a flare (not shown). Alternatively, vessel 40, is isolated from the process flow by means of valve 24 and valve 43, and depressurized through manifold 42, valve 44, manifold 51 to disposal.

During the first stage of regeneration, dry inert gas such as methane, ethane, or nitrogen, which is preferably free of carbon oxides, unsaturated hydrocarbons and hydrogen, is fed from, for example, a nitrogen gas supply system (not shown), through conduit 32, valve 52, and manifold 56, into exchanger 30 to control temperature during regeneration. Effluent from exchanger 30 flows through manifold 31 and, alternately, through valve 38 and manifold 61, or valve 58 and manifold 41, into one of two adsorption vessels 40 and 60, thereby purging gaseous hydrocarbons therefrom to disposal through manifold 62, valve 64, manifold 51, valve 74, and conduit 75, or through manifold 42, valve 44, manifold 51, valve 74, and conduit 75.

During the second stage of regeneration a reducing gas stream predominantly containing hydrogen is fed from, for example, a hydrogen gas supply system (not shown) through conduit 34, valve 54, and manifold 56, into exchanger 30 to control temperature during regeneration. Effluent from exchanger 30 flows through manifold 31 and, alternately, through valve 38 and manifold 61 or valve 58 and manifold 41, into one of two adsorption vessels 40 and 60 to hydrogenate acetylene contained in the bed preferably to ethylene. Effluent from the adsorption vessel during hydrogenation flows therefrom to intermediate storage (not shown) through manifold 62, valve 68, and conduit 73, or through manifold 42, valve 44, manifold 51, valve 66 and conduit 73.

Where heating of the regeneration gas is desired, rates of temperature increase during the second stage of regeneration are preferably controlled to rates of less than about 11° C. per minute (about 20° F. per minute) while increasing the temperature in a range of from about 4° C. to about 200° C. (about 40° F. to about 400° F.). Pressures of the hydrogen-rich reducing gas during the second stage of regeneration are advantageously in a range from about 5 psig to about 500 psig. While the reducing gas is flowing through the adsorbent bed, effluent gas composition is periodically monitored with gas analyzer 80. Second stage regeneration is complete when C2+ hydrocarbon levels in the effluent gas from the bed have been reduced to C2+ hydrocarbon levels in the feed.

Third stage regeneration involves purging all gaseous hydrogen from the adsorption vessel with an inert gas, e.g. nitrogen with or without a saturated hydrocarbon gas such as methane or ethane, while the vessel is at temperatures in a range upwyard from about 140° F. This involves blocking valve 54 and opening valve 52 to switch from hydrogen to inert gas flow through the vessel. After the effluent gas is free of hydrogen, the effluent is directed to flare through manifold 62 via valves 64 and 74, or manifold 42 via valve 44 and valve 74. During this third stage of regeneration flow of inert gas, at or below ambient temperature and about 5 to about 100 psig, cools the vessel to about ambient temperature thereby completing the regeneration process.

Surface area of adsorbents can be determined by the Brunaur-Emmett-Teller (BET) method, or estimated by the simpler Point B method. Adsorption data for nitrogen at the liquid nitrogen temperature, 77 K, are usually used in both methods. The Brunaur-Emmett-Teller equation, which is well known in the art, is used to calculate the amount of nitrogen for mono-layer coverage. The surface area is taken as the area for mono-layer coverage based on the nitrogen molecular area, 16.2 square Angstroms, obtained by assuming liquid density and hexagonal close packing. In the Point B method, the initial point of the straight portion of the Type II isotherm is taken as the completion point for the monolayer. The corresponding amount adsorbed multiplied by molecular area yields the surface area.

Dispersion and surface area of active metal sites was determined by carbon monoxide chemisorption using a Pulse Chemisorb 2700 (Micromeritics). In this procedure, approximately 4 gram samples were purged with helium carrier gas, calcined in air at 500° C. for 1 hr, purged with helium, reduced in hydrogen at 500° C., purged with helium, and cooled to room temperature. The sample was treated with 49.5 percent carbon monoxide in helium and then dosed with 0.045 mL pulses of 49.5 percent carbon monoxide (CO), balance nitrogen, and the carbon monoxide uptake was measured by a thermal conductivity cell. Palladium dispersion values were calculated assuming one carbon monoxide molecule per palladium atom. Palladium loadings are weight percent palladium metal.

In characterizing the pore volume, both total pore volume and its distribution over the pore diameter are needed. The total pore volume is usually determined by helium and mercury densities or displacements. Helium, because of its small atomic size and negligible adsorption, gives the total voids, whereas mercury does not penetrate into the pores at ambient pressure and gives inter-particle voids. The total pore volume equals the difference between the two voids.

Palladium on a high-surface-area $\gamma$-$Al_2O_3$ is a preferred adsorbent for purification of olefins in accordance with this invention. In order to introduce palladium and/or other suitable metal ions on a high-surface-area $\gamma$-$Al_2O_3$, any known technique for monolayer dispersion can be employed. The phenomenon of spontaneous dispersion of metal oxides and salts in monolayer or submonolayer forms onto surfaces of inorganic supports with high surface areas has been studied extensively in the literature (e.g., Xie and Tang, 1990).

EXAMPLES OF THE INVENTION

The following Examples will serve to illustrate certain specific embodiments of the herein disclosed invention. These Examples should not, however, be construed as limiting the scope of the novel invention as there are many variations which may be made thereon without departing from the spirit of the disclosed invention, as those of skill in the art will recognize.

Example 1

A 50 mL TEFLON-lined stainless steel pressure vessel was loaded with 31.99 gm of commercially available adsorbent (about 44 mL of 0.29 percent palladium on $\gamma$-$Al_2O_3$), and a centrally disposed thermocouple system to monitor bed temperatures. After this adsorption vessel was connected into a gas adsorption unit which provided required control of feed gases, temperatures, pressures, and analytical means, the adsorbent bed was run in the down-flow mode. Nitrogen was used to purge the vessel before reducing the oxidized PdO/$\gamma$-$Al_2O_3$ adsorbent by heating to 195° C. in a flow of hydrogen. Electrical heating tape wrapped around the vessel was used to supply heat needed during reduction at 75 psig, with hydrogen flowrates of about 250 mL/min. After 2.5 hours, hydrogen flow was replaced with nitrogen flow. The vessel was cooled to room temperature and immersed in a water recirculating bath to maintain temperature at about 20.5° C. during the subsequent adsorption process.

After analysis of the effluent gases showed that hydrogen had been purged from the vessel, pure ethylene (less than about 0.5 ppm acetylene) was introduced at flow rates of 280 to 300 mL/min from a supply at room temperature. Pure ethylene was allowed to flow through the vessel for 15 min after vessel pressure reached 110 psig, and thereafter the flow of pure ethylene was replaced with a feed mixture which contained 191 ppm acetylene in a balance of ethylene. During adsorption the flow rate of the acetylene/ethylene mixture was 110 mL/min and operating conditions of temperature and pressure were controlled to 110 psig and 20.5° C. By periodical analysis of effluent gas using an on-line gas chromatograph, acetylene was detected (less than about 0.5 ppm acetylene) breaking through the bed of adsorbent after a total of 28 L (1 atm and 21° C.) of feed gas was treated. In this example the adsorbent exhibited a capacity of about 0.12 mL of acetylene per mL of adsorbent.

After flow of the acetylene/ethylene mixture was stopped, the vessel was depressurized to 1 atm and nitrogen was purged through the vessel for about 15 min. The vessel was again wrapped in heating tape and heated to 150° C. Adsorbent was regenerated using pure hydrogen at a flow rate of 250 mL/min at 60 psig in about 13 hours.

Comparative Example

This comparative example is to illustrate the essential role of transition/noble metal in acetylene captation by use of a pure gamma alumina support without any dispersed transition/noble metal. This experiment was carried out using Alcoa F-200 alumina in the form of ⅛" spheres. Another 50 mL TEFLON-lined pressure vessel was loaded with 21.98 gm (31.5 mL) of the Alcoa F-200 alumina, and the vessel was connected into a gas adsorption unit as in Example 1. Nitrogen was used tp purge the vessel and alumina bed which were then heated to 170° C. (about 338° F.) with a flow of hydrogen. A pretreatment hydrogen reduction was run at 15 psig and hydrogen flow rate of about 250 mL/minute. After 3.5 hours the hydrogen pretreatment was stopped by replacing the hydrogen flow with nitrogen flow. The vessel was allowed to cool to about room temperature and then the vessel was immersed in a water recirculating bath to maintain a constant temperature of about 22° C. (about 72° F.).

After nitrogen had purged all hydrogen from the vessel, pure ethylene (<0.5 ppm acetylene) was then introduced at a flow rate of from about 280 to about 300 mL/minute. After several minutes the ethylene pressure in the vessel was increased to 110 psig. Pure ethylene was allowed to flow through the vessel for another 90 minutes before switching to a gas feed mixture containing 191 ppm acetylene in a balance of ethylene.

Flow rate of the acetylene/ethylene mix was 110 mL/minute, and the vessel was at 110 psig and 22° C. (about 72° F.). Gas effluent compositions were taken periodically, using an on-line gas chromatograph to determine when acetylene started breaking through the adsorbent bed. A least 17 ppm of acetylene was observed in the gas effluent after only 18 minutes had elapsed from the time the acetylene/ethylene flow was started. This means the alumina has virtually no captation capacity for acetylene (less than 0.01 mL of acetylene per mL of adsorbent), and that the acetylene captation observed in Example 1 was due to the palladium metal dispersed on the alumina support.

Flow of the gas feed mixture was then stopped, the vessel depressurized to 1 atm, and nitrogen was used to purge the vessel for about 10 to about 15 minutes. Regeneration was then started by flowing pure hydrogen through the vessel at 120 psig, and 250 mL/minute for about 17 hours.

Example 2

This example includes several adsorption cycles to illustrate critical roles of the amount of active metal and its valence state on the carrier for acetylene adsorption from a feed gas mixture containing less than 500 ppm acetylene in a balance of ethylene. Adsorbent for this experiment was prepared by crushing, using a mortar and pestle, ⅛ inch spheres of gamma alumina, loaded with 14 percent by weight of NiO, to particle sizes in the range of 8 on 14 mesh.

Example 2—Cycle A

Another 50 mL TEFLON-lined pressure vessel was loaded with 22.03 gm (31.6 mL) of the 14 percent NiO on gamma alumina, and the vessel was connected into a gas adsorption unit as in Example 1. Nitrogen was used to purge the vessel and bed of adsorbent which were then heated to temperatures in the range of from 140° C. to 250° C. with a flow of hydrogen. A pretreatment hydrogen reduction was run at 55 psig and hydrogen flow rate of about 250 mL/minute. After 3 hours the hydrogen pretreatment was stopped by replacing the hydrogen flow with nitrogen flow. The vessel was allowed to cool to about room temperature and then immersed in a water recirculating bath to maintain a constant temperature of about 21.5° C.

After nitrogen had purged all hydrogen from the vessel, pure ethylene (<0.5 ppm acetylene) was then introduced at a flow rate of from about 280 to about 300 mL/minute. After several minutes the ethylene pressure in the vessel was increased to 110 psig. Pure ethylene was allowed to flow through the vessel for another 90 minutes before switching to a gas feed mixture containing 191 ppm acetylene in a balance of ethylene.

Flow rate of the acetylene/ethylene feed mixture was 114.5 mL/minute and pressure in the vessel was at 103 psig. Effluent compositions were taken periodically using an on-line gas chromatograph to determine when acetylene started breaking through the adsorbent bed. Only 16 minutes after starting flow of acetylene/ethylene feed, acetylene was observed in the effluent at about 11 ppm. Therefore, the NiO/alumina was not able to satisfactorily remove acetylene from the ethylene feed with the hydrogen reduction of only 3 hours.

Example 2—Cycle B

Hydrocarbon flow was stopped, the vessel depressurized to 1 atm and purged with nitrogen for 10 to 15 minutes. Another regeneration was then started by flowing pure hydrogen through the vessel at 65 psig and 250 mL/minute. During this hydrogenation/regeneration the vessel was again at about 226° C. After about 16 hours of this treatment the vessel was cooled in a nitrogen purge.

A second acetylene/ethylene adsorption was carried out in the same manner as the first adsorption described in this example. Acetylene was detected in effluent from the adsorbent bed by the very first on-line GC analysis indicating minimal acetylene adsorption capacity. Another 16 hour hydrogen reduction cycle was performed at 65 psig and 226° C. After stopping the hydrogen and purging the vessel with nitrogen, it was cooled to 9.5° C. A third acetylene/ethylene adsorption was carried out at 9.5° C. and 100 psig. This time the Ni/Al$_2$O$_3$ adsorbent was able to remove all the acetylene from the ethylene feed that contained 243 ppm acetylene. The adsorption capacity was 0.0923 mL acetylene/mL of adsorbent.

It should be noted that small amounts of butenes and butadiene were also observed in the effluent when the acetylene/ethylene mixture was flowed through the adsorbent bed. This is an indication that the 14 percent NiO on alumina adsorbent caused oligomerization of acetylene and thereby formed "green oil" or unsaturated polybutadiene type polymers. Green oil formation can not be tolerated where adsorbent is used to purify polymer-grade ethylene.

Example 2—Cycle C

After a 14 hour regeneration using hydrogen at 65 psig, and temperatures varying from 200° C. to 268° C. the adsorbent bed underwent another ethylene/acetylene adsorption cycle. The adsorbent bed was held at 21.8° C. using a water recirculating bath, and the feed gas contained 243 ppm acetylene in ethylene. Feed gas pressure was 103 psig and the gas flow rate was 112.2 mL/minute. Acetylene did not break through the adsorbent bed until about 1.5 hour after the acetylene/ethylene feed flow was started. This corresponded to about 0.02 mL acetylene adsorbed per mL of adsorbent. During the adsorption cycle small amounts of butenes and butadiene were also detected in the effluent, indicating green oil was being formed using this 14 percent NiO on alumina adsorbent.

Example 3

This example includes several adsorption cycles to illustrate critical roles of temperature and pressure on adsorbent capacity for acetylene adsorption from a feed gas mixture containing less than 500 ppm acetylene in a balance of ethylene. These runs were conducted at various preselected temperatures and pressures using a Pd/Al$_2$O$_3$ adsorbent, and illustrated how significantly acetylene adsorption capacity was affected. The Pd/Al$_2$O$_3$ adsorbent (0.3 percent palladium by weight) was prepared as in Example 2.

Temperature at which adsorption occurs is believed to have an effect on both the adsorption capacity and the extent of undesirable side reactions such as green oil formation or acetylene/ethylene decomposition.

In six consecutive runs, three adsorption temperatures were studied, 7.4° C., 22° C. and 48.4° C. All other variables were held constant, including; ethylene containing about 210 ppm acetylene, feed flow rate at 198 mL/min, pressure at 200 psig, and the same 43 mL bed of Pd/Al$_2$O$_3$ adsorbent (0.23 percent palladium by weight). Between cycles the adsorbent was egenerated with tail gas containing about 21 percent hydrogen, 5 percent ethylene, 300 ppm carbon monoxide, and balance of methane at 120° F. (about 49° C.) and 80 psig for several hours. TABLE 1 reports average acetylene adsorption capacity in units of mL acetylene adsorbed per mL of bed at the three temperature of adsorption.

TABLE 1

| Temperature, ° C. | Capacity* |
|---|---|
| 48.3 | 0.330 |
| 23.0 | 0.268 |
| 7.4 | 0.248 |

*Capacity in mL acetylene adsorbed per mL of bed

Example 4

As this example illustrates, pressure has a minor effect on adsorption capacity of acetylene on another $Pd/Al_2O_3$ adsorbent (0.3 percent palladium by weight). Only a minimal increase in the adsorption capacity was observed with increasing gas pressure during the adsorption cycle.

Six laboratory runs were carried out at three different pressures: 100, 200 and 300 psig. Two runs were done at each pressure to provide an average. All other variables were kept constant, including ethylene feed containing 218 ppm acetylene, temperature at 120° F., feed flow rate at 198 mL/min, and the same 44 mL (31.6 gms) bed of the $Pd/Al_2O_3$ adsorbent. Table 2 reports average acetylene adsorption capacity at the three pressures studied.

There is a slight increase in acetylene adsorption capacity with increasing pressure. Data was also obtained using a larger unit connected to a polymer grade ethylene pipeline that operated at over 1800 psig. The adsorption capacity was between 0.0204 to 0.0215 lb acetylene/cu ft adsorbent, which is similar to what was observed at about 300 psig in the laboratory apparatus.

TABLE 2

| Pressure, psig | Capacity* |
|---|---|
| 100 | 0.24 |
| 200 | 0.30 |
| 300 | 0.32 |

*Capacity in mL acetylene adsorbed per mL of bed

Example 5

Pure hydrogen has been shown in the previous examples to work well in regenerating the acetylene-saturated $Pd/Al_2O_3$ adsorbent. In a commercial olefins unit however, pure hydrogen is a valued and limited stream. Tail gas, which comprises 15 to 35 percent hydrogen, 0.1 to 5 percent ethylene, 100 to 500 ppm CO, and the balance methane, is more plentiful and less expensive relative to pure hydrogen at an olefins unit. This example illustrates that use of tail gas to regenerate an acetylene saturated adsorbent bed is as effective as pure hydrogen.

Example 6—Cycle A

A 31.96 gm (43 mL) of another $Pd/Al_2O_3$ adsorbent (0.3 percent palladium by weight) was reduced using pure hydrogen as in Example 1, with the exception that the reduction temperature was held at 180° C., at 75 psig for 7 hours. After stopping the hydrogen reduction and cooling the vessel to about 49° C. (120° F.) in nitrogen, a stream containing 191 ppm acetylene, balance ethylene gas, was passed through the adsorbent bed at 110 psig. Upon acetylene breakthrough, the vessel was then depressurized and purged with nitrogen. Acetylene adsorption capacity was 0.06 mL acetylene/mL adsorbent. Regeneration was then done with pure hydrogen at 75 psig, about 49° C. (120° F.), at 250 mL/min. After regeneration the $Pd/Al_2O_3$ bed was exposed to another acetylene/ethylene adsorption cycle and the acetylene capacity was 0.062 mL acetylene/mL adsorbent.

Example 6—Cycle B

The next regeneration cycle was done using a gas blend containing 21.32 mole percent hydrogen, 0.1440 mole percent ethylene, 0.101 mole percent carbon monoxide, with the balance being methane.

Tail gas was introduced at a flow rate of about 200 mL/minute and 75 psig. Temperature was held at about 49° C. (120° F.) for the regeneration by immersing the adsorption vessel in a water bath. After about 16 hours, flow of tail gas was stopped, and nitrogen was used to purge the vessel for 30 minutes at about 49° C. (120° F.). Pure ethylene was then flowed through the vessel at 110 psig for about 1.5 hours at 110 mL/minute flow. After this time, the 191 ppm acetylene/ethylene mixture was flowed through the reactor at 110 psig, 120° F., and 110 mL/minute flow rate. After about 4.5 hours acetylene was detected in the bed effluent, which corresponds to 0.0977 mL/acetylene adsorbed/mL of adsorbent, surpassing the adsorption capacity observed when pure hydrogen was used for regeneration.

Example 6—Cycle C

Tail gas was used again to regenerate the adsorbent bed at the same conditions as above, only that instead of 16 hours of regeneration, only 2.75 hours of regeneration was done. When exposed to another ethylene/acetylene adsorption cycle, acetylene adsorption capacity was 0.089 mL acetylene/mL adsorbent, nearly the same as when a 16 hour regeneration was done. No deleterious green oil was formed when tail gas was used for regeneration, and the adsorption capacity actually increased compared to pure hydrogen.

Example 7

Larger scale testing was done at a commercial olefin steam cracking plant to demonstrate this invention under more severe conditions such as pipeline ethylene pressures of 1800 psig, ethylene flow rates in the 100 to 700 lb/hr range, and temperatures of about 27° C. to about 49° C. (80° F. to 120° F.).

The test unit consisted of a down flow reactor vessel that contained 1 $ft^3$ of a palladium on gamma alumina adsorbent (0.32 percent palladium by weight). Polymer-grade ethylene, which contained less than 1 ppm acetylene at 1800 psig, was the olefin feed. For reduction and regeneration of the adsorbent, ambient temperature tail gas was used which contained about 42 percent hydrogen, 0.8 to 5 percent ethylene, 300 to 500 ppm carbon monoxide and the balance methane. The fresh adsorbent was reduced with a 110 lb/hr flow rate of tail gas at 63 psig for about 18 hours. Temperatures increased from inlet to outlet of the bed about 30° C. to 40° C. (about 86° F. to 104° F.) due to the heat of hydrogenation of ethylene in the tail gas. After the reduction cycle flow of tail gas was stopped, nitrogen was used to purge the vessel to remove all hydrogen from the adsorbent. The vessel was then pressurized with 300 to 500 psig nitrogen, followed by a slow pressurization of the vessel with the 1800 psig ethylene stream. Once the vessel was at ethylene feed pressure of 1800 psig, the flow rate was adjusted to about 100 lbs/hr.

Analysis of effluent ethylene indicated less than 20 parts per billion (ppb) acetylene, while 0.2 to 0.65 ppm acetylene was in the feed ethylene. Flow rates were increased to 600–700 lbs/hr and held there until about 58,000 lbs of ethylene had flowed through the adsorbent bed. A slight breakthrough of 0.08 ppm acetylene was then detected in the effluent. The ethylene flow was stopped and the vessel depressurized and purged with nitrogen for ½ hour. Acetylene adsorption capacity was about 0.305 mL acetylene adsorbed per mL of bed.

Regeneration was done using tail gas at ambient temperature and 63 psig. About 4 hours of tail gas flow through the bed at 110 lbs/hr was enough to regenerate the 1 ft$^3$ bed of adsorbent. Tail gas was then stopped, nitrogen was used to purge the unit for ½ hour, and the next ethylene/acetylene adsorption cycle started.

The second ethylene/acetylene adsorption cycle was done under identical conditions as the first cycle above, except the feed flow rate was constant at 400 lbs/hr. After over 66,000 lbs of ethylene was treated, a small amount 0.06 ppm of acetylene started to break through the bed. This corresponds to an adsorption capacity of about 0.32 mL acetylene adsorbed per mL of bed.

Example 8
Preparation of Cu/Al$_2$O$_3$ Adsorbent

In this preparative example an incipient wetness method of impregnation was used to prepare the Cu/Al$_2$O$_3$ adsorbent. Cupric nitrate (Fischer 98.3 percent), 15.27 gm, was dissolved in 75.1 mL of deionized water. The blue-green solution was slowly added to 83.42 gm of dried Alcoa F-200 activated alumina spheres (1/16 inch) with stirring, using a magnetic stir bar and stir plate. Just enough solution was added to the alumina in order for it to reach it's wetness point. Wet adsorbent was then heated on a hot plate at low heat with constant stirring to remove excess moisture. The adsorbent was then transferred to a 250 mL round bottom flask connected to a vacuum line and heated to about 90° C. under vacuum to further dry it. After a few hours the blue, dried adsorbent was transferred to a clay crucible for calcination in air to 600° C. for 12 hours using an electric muffle furnace. After allowing the adsorbent to cool to room temperature, it was removed from the furnace and stored in a vacuum desiccator. The adsorbent was a green color. Metals analyses indicated 4.1 percent copper by weight was on the alumina, and the depth of copper penetration into the pellet was about 1 mm. Analysis using XRD line broadening showed the supported copper particles to be around 30 Angstroms. BEF surface area of the alumina spheres was over 220 m$^2$/gm.

A bed of about 43 mL (31.35 gm) of the calcined 4.1 percent CuO/Al$_2$O$_3$ adsorbent was placed in the 50 mL stainless steel vessel between glass wool plugs. The vessel was attached to the adsorption unit as described in Example 1. Electric heat tape and insulation were wrapped around the vessel while purging the vessel with nitrogen at room temperature. It is important to reduce the copper oxide to copper metal. Where Cu(I) and/or Cu (II) are contacted with acetylene there is a likely possibility that explosive copper (I), (II) acetylides would be formed. In order to reduce the copper oxide to copper metal (0 oxidation state) a mixture of hydrogen and nitrogen was then flowed through the vessel while monitoring the bed temperatures. Hydrogen concentration of the mixture was slowly increased so as to avoid a large exotherm in the bed during reduction of the copper. Eventually, pure hydrogen was flowed through the reactor at room temperature. The vessel was then heated over a period of 3 hours to 200° C. while flowing pure hydrogen through it. The bed was then held at 200° C. in flowing hydrogen overnight (17 hours) before shutting off the hydrogen and purging the reactor with nitrogen. The bed was then cooled to room temperature.

Example 8—Cycle A
Acetylene Adsorption

After the Cu/Al$_2$O$_3$ bed cooled to 25° C. under a nitrogen atmosphere, at 190 mL/min flow of 214 ppm acetylene in ethylene gas was introduced to the vessel at 15 psig. Temperature increased to 32.1° C. for a few minutes due to the heat of adsorption of ethylene, and then returned to room temperature. To control temperature the vessel was immersed in a water bath which was held at 25° C.

The acetylene content in the effluent ethylene gas was analyzed periodically using an on-line gas chromatograph. No detectable acetylene (<0.5 ppm) was observed, indicating total adsorption of the feed acetylene onto the reduced Cu/Al$_2$O$_3$ bed. As the day progressed, the gas feed flow was increased to 350 mL/min and yet no acetylene breakthrough was observed in the effluent. After 9 hours of gas adsorption the bed still had not broken through acetylene. Hydrocarbon flow was stopped and a nitrogen purge was initiated at pressure of 1 atmosphere to remove hydrocarbon from the vessel. Acetylene adsorption corresponded to 0.624 mL acetylene/mL adsorbent, although no breakthrough occurred.

Regeneration of the Acetylene—Cu/Al$_2$O$_3$ bed.

Even though the above experiment did not have an acetylene breakthrough, a regeneration was attempted using pure hydrogen at 49° C., and 50 psig. To avoid any large exotherm, the hydrogen regeneration gas was slowly added to a nitrogen purge. Once hydrogen flow reached 250 mL/min. the nitrogen purge was shut off such that pure hydrogen was flowing over the adsorbent. After 21 hours of pure hydrogen flow (250 mL/min.) at 50 psig and 49° C., the hydrogen was shut off and the vessel purged with nitrogen. Using a water bath, the vessel was then cooled to 25° C. and another acetylene/ethylene adsorption cycle started.

Example 8—Cycle B

Since no breakthrough was observed during the first cycle, a higher acetylene/ethylene feed flow rate of 407 mL/min was used while pressure was held at 15 psig, and temperature was 25° C.; Yet, after 9 hours at this high flow rate, there was no sign of acetylene breakthrough in the effluent. The bed adsorbed 1.03 mL acetylene/mL adsorbent. Another regeneration with pure hydrogen was conducted at 49° C., and 50 psig for 24 hours.

Example 8—Cycle C

After regeneration, the reduced Cu/Al$_2$O$_3$ bed was purged with nitrogen for ½ hour before 214 ppm acetylene/ethylene feed was introduced to the vessel. An even higher gas flow rate was used (500 mL/min) in order to try to reach acetylene breakthrough in a 9 hour period. This flow rate was near the maximum this laboratory unit could produce. Yet after another 9 hours of acetylene/ethylene flow at 25° C., 15 psig, there was still no sign of acetylene breakthrough. The acetylene adsorbed was now 1.27 mL/mL adsorbent. It was clear that the amount of Cu/Al$_2$O$_3$ adsorbent in the bed would have to be decreased in order to reach breakthrough. The used adsorbent was then regenerated with pure hydrogen at 49° C., and 50 psig for 12 hours. After this regeneration, the reduced Cu/Al$_2$O$_3$ was cooled to 10° C. and then slowly oxidized by introducing small pulses of air into the nitrogen purge stream. The exotherms from the oxidation were kept to below 5° C. Eventually a continuous stream of air could be flowed through the vessel with no nitrogen diluent. After warming the vessel up to room temperature, the used adsorbent was removed. It was a dark gray color with a slight hint of red on some pellets. There was no shock sensitivity of these pellets, as was determined by grinding them into dust with a mortar and pestle. X-ray analysis showed no sign of copper acetylide phases in the used catalyst, only 30 Angstrom copper particles that were a mixture of metallic and oxidized copper were detected.

Example 9

In order to achieve acetylene breakthrough in a timely manner, the amount of adsorbent was reduced by blending 20 mL of the $Cu/Al_2O_3$ adsorbent with 23 mL of inert alumina pellets. Adsorbent volume in the bed was reduced to less than half the amount in Example 8. This blended adsorbent bed was then reduced with pure hydrogen at 200° C. for several hours, as described above. Once reduced, the $Cu/Al_2O_3$ was purged with nitrogen.

Example 9—Cycle A

Ethylene feed containing 214 ppm acetylene was then flowed through the bed at 25° C., 15 psig, at a flow rate of 497 mL/min. Effluent samples taken periodically indicated total acetylene removal from the feed. After about 9 hours on stream, the flow was stopped even though no acetylene breakthrough was observed. The $Cu/Al_2O_3$ had adsorbed 2.41 mL acetylene/mL adsorbent. After a ½ hour nitrogen purge, the adsorbent was regenerated with pure hydrogen at 49° C. and 250 mL/min. flow at 50 psig. The hydrogen regeneration was stopped after 14.7 hours and a nitrogen purge was introduced to the unit.

Example 9—Cycle B

A second adsorption cycle was then begun at the maximum feed gas flow possible, 560 mL/min, of ethylene feed containing 214 ppm acetylene. Process conditions were otherwise the same, at 25° C. and 15 psig. Again, no acetylene breakthrough was observed after 9 hours of flow. The acetylene adsorption capacity was over 2.7662 mL acetylene/mL adsorbent! Clearly the bed would need to be diluted again with alumina in order to achieve breakthrough.

Example 10

More alumina dilution was needed to achieve acetylene breakthrough in a timely manner. Therefore, 10 mL (7.0 gm) of the 4.1% $Cu/Al_2O_3$ adsorbent was mixed with 33 mL (25.19 gm) of alumina ⅛ inch spheres.

The mixture was loaded into the 50 mL vessel used in the above examples. After purging with nitrogen for 1 hour, hydrogen was slowly mixed in with the nitrogen feed at room temperature and 1 atm pressure. Eventually all the nitrogen flow was stopped and only pure hydrogen was flowing over the catalyst. The vessel was then heated to 200° C. in a 250 mL/min flow of hydrogen at 1 atm for 17.85 hours in order to reduce the copper oxide to copper metal. The hydrogen flow was then stopped while the vessel was at 200° C. and a nitrogen purge was started. Heating was stopped and the vessel allowed to cool to 25° C. by immersing it in a water bath.

Example 10—Cycle A

Ethylene feed containing 214 ppm acetylene was then flowed through the reduced $Cu/Al_2O_3$ bed at 500 mL/min at 15 psig and 25° C. No acetylene breakthrough was observed until 8.5 hours later when about 1 ppm acetylene broke through the bed. Calculated acetylene adsorption capacity of this $Cu/Al_2O_3$ adsorbent was 5.42 mL acetylene/mL adsorbent.

Example 10—Cycle B

Hydrogen regeneration was carried out at 49° C. and 50 psig, for 23 hours at a flow rate of 250 mL/min. After regeneration the vessel was purged with nitrogen before starting another acetylene/ethylene adsorption cycle. Ethylene feed containing 214 ppm acetylene was used at a higher flow rate of 558.5 mL/min, at 15 psig and 25° C. Acetylene breakthrough was again observed after several hours on stream, and the resulting acetylene capacity was 1.98 mL acetylene/mL adsorbent. This cycle demonstrated that regeneration with hydrogen, according to the invention, does indeed regenerate an acetylene saturated, reduced $Cu/Al_2O_3$ bed.

Example 10—Cycle C

Another hydrogen regeneration was for 15 hours at the same conditions described above. After regeneration and nitrogen purging, another acetylene/ethylene adsorption cycle was started. An acetylene capacity of 1.14 mL acetylene/mL adsorbent was reached before breakthrough, again demonstrating regeneration according to the invention of an acetylene saturated $Cu/Al_2O_3$ bed. A higher temperature (85° C. to 80° C.) hydrogen regeneration was then done and the next adsorption cycle demonstrated a 1.2 mL acetylene/mL adsorbent capacity. Another hydrogen regeneration was then done at an even higher temperature (about 150° C.) and the next adsorption cycle again demonstrated a 1.4 mL acetylene/mL adsorbent capacity.

For the purposes of the present invention, "predominantly" is defined as more than about fifty per cent. "Substantially" is defined as occurring with sufficient frequency or being present in such proportions as to measurably affect macroscopic properties of an associated compound or system. Where the frequency or proportion for such impact is not clear, substantially is to be regarded as about twenty per cent or more. The term "essentially" is defined as absolutely except that small variations which have no more than a negligible effect on macroscopic qualities and final outcome are permitted, typically up to about one percent.

Examples have herein been presented and hypotheses advanced in order to better communicate certain facets of the invention. The scope of the invention is determined solely by the scope of the appended claims.

That which is claimed is:

1. A process for purification of olefins which comprises:
    passing a gaseous mixture comprising a hydrocarbon of from 2 to about 8 carbon atoms including at least one vinyl group, acetylenic impurities having the same or similar carbon content and, optionally, saturated hydrocarbon gases through a particulate bed of adsorbent comprising predominantly a support material having high surface area on which is dispersed at least one metallic element in the zero valent state selected from the group consisting of copper and silver to effect, in the presence of an essentially dihydrogen-free atmosphere within the bed, selective and reversible adsorption and/or complexing of the contained acetylenic contaminants with the adsorbent, and thereby obtain purified effluent which contains less than about 1 parts per million by volume of the acetylenic impurities; and
    thereafter regenerating the resulting bed of adsorbent in the presence of a reducing gas comprising dihydrogen to effect release of the contained acetylenic impurities from the adsorbent.

2. The process according to claim 1 wherein the metallic element is dispersed on the high surface area support material in particles having average diameter in a range of less than about 200 Angstroms.

3. The process according to claim 2 wherein the gaseous mixture passes through the bed of particulate adsorbent at gas hourly space velocities in a range of from about 0.05 hours$^{-1}$ to about 20,000 hours$^{-1}$ measured at standard conditions of 0° C. and 760 mm Hg.

4. The process according to claim 1 wherein the adsorbent comprises at least about 90 weight percent of a gamma alumina having surface area in a range of from about 80 to about 500 square meters per gram as measured by the BET gas adsorption method, and contains less than 500 parts per million by weight of a sulfur-containing component calculated as elemental sulfur.

5. The process according to claim 4 wherein the metal dispersed on the support material is copper, and the absorbent has a copper content in a range of from about 0.01 to about 10 percent based on the total weight of the adsorbent.

6. The process according to claim 1 wherein the olefin in the gaseous mixture being purified is predominantly ethylene or propylene, the gaseous mixture contains less than about 0.5 parts per million by volume of dihydrogen and less than about 1 parts per million by volume of mercury-containing, arsenic-containing, and sulfur-containing components, each calculated as the element, and wherein the gaseous mixture, while passing through the bed, is at temperatures in a range of from about −35° C. to about 65° C.

7. The process according to claim 6 wherein the adsorbent comprises at least about 90 weight percent of a gamma alumina having surface area in a range of from about 150 to about 350 square meters per gram as measured by the BET gas adsorption method, and wherein the metal dispersed on the support material is copper, and the absorbent has a copper content in a range of from about 0.01 to about 10 percent based on the total weight of the adsorbent.

8. The process according to claim 1 wherein the adsorbent has a metal dispersion value of at least 10 percent as measured by carbon monoxide chemisorption method.

9. A process for purification of olefins produced by thermal cracking of hydrocarbons which comprises:

passing a gaseous mixture comprising at least about 99 percent by volume of an olefin having from 2 to about 4 carbon atoms, and acetylenic impurities having the same or similar carbon content in an amount in a range upward from about 1 to about 1000 parts per million by volume, through a particulate bed of adsorbent comprising predominantly a support material selected from the group alumina, silica, active carbon, clay and zeolites having surface area in a range of from about 10 to about 2,000 square meters per gram as measured by the BET gas adsorption method, on which is dispersed at least one metallic element in the zero valent state selected from the group consisting of copper, silver, iron, cobalt, nickel, zinc, ruthenium, palladium, and platinum, to provide an effluent stream from the bed;

effecting, in the presence of an essentially dihydrogen-free atmosphere within the bed, selective and reversible adsorption and/or complexing of the contained acetylenic impurities with the adsorbent, until levels of the acetylenic impurities in the effluent stream increase to a limiting level in a range downward from about 1 parts per million by volume; and thereafter regenerating the resulting bed of adsorbent in the presence of a reducing gas comprising dihydrogen to effect release of the contained acetylenic impurities from the adsorbent.

10. The process according to claim 9 wherein the adsorbent comprises a-dispersion-of-copper or silver and further comprises at least one element selected from the group consisting of lithium, sodium, potassium, molybdenum, tin, tungsten, and iridium, dispersed on the support material.

11. The process according to claim 9 wherein the support is a material selected from the group consisting of alumina, silica, carbon, clay and zeolites, and has a surface area in a range of from about 10 to about 2,000 square meters per gram as measured by the BET gas adsorption method.

12. The process according to claim 9 wherein the metal dispersed on the support material is at least one element selected from the group consisting of copper and silver, and the adsorbent has a dispersed metal content in a range of from about 0.01 to about 10 percent based on the total weight of the adsorbent.

13. The process according to claim 12 wherein the gaseous mixture passes through the bed of particulate adsorbent at space velocities in a range of from about 0.05 hours$^{-1}$ to about 20,000 hours$^{-1}$ measured at standard conditions of 0° C. and 760 mm Hg.

14. The process according to claim 13 wherein the metal dispersed on the support material is copper, and the adsorbent has a copper content in a range of from about 0.01 to about 10 percent based on the total weight of the adsorbent.

15. The process according to claim 9 wherein the olefin in the gaseous mixture being purified is predominantly ethylene or propylene, the gaseous mixture contains less than about 0.5 parts per million by volume of dihydrogen and less than about 1 parts per million by volume of mercury-containing, arsenic-containing, and sulfur-containing components, each calculated as the element, and wherein the gaseous mixture, while passing through the bed, is at temperatures in a range of from about minus 35° C. to about 65° C.

16. The process according to claim 15 wherein the adsorbent comprises at least about 90 weight percent of a gamma alumina having surface area in a range of from about 150 to about 350 square meters per gram as measured by the BET gas adsorption method, and wherein the metal dispersed on the support material is palladium, and the adsorbent has a palladium content in a range of from about 0.01 to about 10 percent based on the total weight of the adsorbent.

17. The process according to claim 9 wherein the adsorbent has a metal dispersion value in a range upward from about 20 percent to about 80 percent as measured by carbon monoxide chemisorption method.

18. The process according to claim 2 wherein the adsorbent further comprises at least one element selected from the group consisting of lithium, sodium, potassium, zinc, molybdenum, tin, tungsten, and iridium, dispersed on the support material.

19. The process according to claim 2 wherein the support is a material selected from the group consisting of alumina, silica, active carbon, clay and zeolites, and has surface area in a range of from about 10 to about 2,000 square meters per gram as measured by the BET gas adsorption method.

20. The process according to claim 19 wherein the metal dispersed on the support material is copper, and the adsorbent has a dispersed metal content in a range of from about 0.01 to about 10 percent based on the total weight of the adsorbent.

* * * * *

UNITED STATES PATENT AND TRADEMARK OFFICE
CERTIFICATE OF CORRECTION

Page 1 of 2

PATENT NO. : 6,124,517
DATED : September 26, 2000
INVENTOR(S) : Mark P. Kaminsky, et. al.

It is certified that error appears in the above-identified patent and that said Letters Patent is hereby corrected as shown below:

| Col. | Line | | |
|------|------|---|---|
| 4 | 23 | "polyethylene and proypropylene," should read: "polyethylene and polypropylene," -- | |
| 19 | 46 | "BEF surface area of the" should read: "BET surface area of the" | |
| 23 | 19,20 | "the absorbent has a copper" should read: "the adsorbent has a copper" | |
| 23 | 36 | "and the absorbent has a" should read: "and the adsorbent has a" | |

UNITED STATES PATENT AND TRADEMARK OFFICE
CERTIFICATE OF CORRECTION

PATENT NO. : 6,124,517
DATED : September 26, 2000
INVENTOR(S) : Mark P. Kaminsky, et. al.

It is certified that error appears in the above-identified patent and that said Letters Patent is hereby corrected as shown below:

23   38   "weight ofthe adsorbent."

should read:
"weight of the adsorbent."

Signed and Sealed this

Twenty-second Day of May, 2001

Attest:

NICHOLAS P. GODICI

Attesting Officer     Acting Director of the United States Patent and Trademark Office